United States Patent [19]

Fay et al.

[11] Patent Number: 4,558,144

[45] Date of Patent: Dec. 10, 1985

[54] VOLATILE METAL COMPLEXES

[75] Inventors: Robert C. Fay, Ithaca; David A. Thompson, Big Flats, both of N.Y.

[73] Assignee: Corning Glass Works, Corning, N.Y.

[21] Appl. No.: 662,829

[22] Filed: Oct. 19, 1984

[51] Int. Cl.$^4$ .............................................. C07F 3/06
[52] U.S. Cl. ..................................... 556/40; 568/412; 427/252
[58] Field of Search .......................... 260/429.9, 429 J; 568/412

[56] References Cited

U.S. PATENT DOCUMENTS 4,015,980  4/1977  MacKay ...................... 260/429.9 X
4,424,352  1/1984  Siedle .......................... 260/429 J X
4,425,281  1/1984  Doyle .......................... 260/429 J X

OTHER PUBLICATIONS

Mehrotra et al., Metal $\beta$-Diketonates and Allied Derivatives, Academic Press, N.Y., pp. 42 to 45, (1978).
Chemical Abstracts 83 157284g, (1975).
Chemical Abstracts 82 103787j, (1974).
Chemical Abstracts 83 137659e, (1975).
Chemical Abstracts 76 28261d, (1971).
Chemical Abstracts 82 103787j, (1974).
Chemical Abstracts 73 92153k, (1969).

*Primary Examiner*—Helen M. S. Sneed
*Attorney, Agent, or Firm*—K. van der Sterre

[57] ABSTRACT

Novel adducts of magnesium and zinc $\beta$-diketonates with the bidentate ether 1,2-dimethoxyethane are disclosed which exhibit high vapor pressures upon moderate heating, and improved resistance to thermal decomposition at vaporization temperatures.

3 Claims, 6 Drawing Figures

4,558,144

VOLATILE METAL COMPLEXES

BACKGROUND OF THE INVENTION

The present invention relates to organometallic compounds, and particularly relates to β-diketonate complexes of magnesium and zinc which exhibit a combination of high volatility and good thermal stability.

Volatile metal complexes are of interest for a variety of applications including fuel additives, metal vapor sources, and gas transport reagents. A useful discussion of β-diketonate complexes and their uses is provided by R. E. Sievers et al. in *Science*, 201 [4352], pages 217–223 (July 1978), wherein numerous references to these complexes and methods for their preparation are cited.

The metal complexes or chelates of the anion of hexafluoroacetylacetone(1,1,1,5,5,5,-hexafluoro-2,4-pentanedione), the anion having the formula $[CF_3-CO-CH-CO-CF_3]^-$ and hereinafter abbreviated $(hfa)^-$, have been the objects of specific study. For example, the complexes $Cd(hfa)_2$, $Mg(hfa)_2$ and $Zn(hfa)_2$ are known, although these complexes are most frequently isolated as adducts with Lewis bases that are dissolved in the solvents used in their preparation, such as $H_2O$ and $NH_3$. Thus the adducts $Cd(hfa)_2 \cdot NH_3 \cdot H_2O$, $Cd(hfa)_2 \cdot 2H_2O$ and $Zn(hfa)_2 \cdot 2H_2O$, the latter being characterized as hydrates, have been reported by S. C. Chattoraj et al. in *J. Inorg. Nucl. Chem.*, 28, pages 1937–1943 (1966).

European patent application EP No. 0103446 describes metal diketonate adducts of the formula $M(hfa)_2 \cdot nTHF$, wherein M is Mg or Zn and n is 1–4, which exhibit good thermal stability and volatility. As reported in that application, the magnesium complex $Mg(hfa)_2 \cdot 2THF$ can be volatilized without decomposition at 200° C. However, complexes of even higher volatility and thermal stability are still being sought.

SUMMARY OF THE INVENTION

The present invention provides novel complexes of magnesium or zinc which exhibit improved thermal stability and volatility. The complexes of the invention are adducts with 1,2-dimethoxyethane(1,2-DME) of magnesium or zinc hexafluoroacetylacetonates.

Complexes provided in accordance with the invention have the molecular formula: $M(hfa)_2 \cdot 1,2\text{-DME}$ wherein M is Zn or Mg, and wherein 1,2-DME represents a single 1,2-dimethoxyethane ligand forming a 1:1 adduct with the $M(hfa)_2$ molecule. These adducts exhibit not only higher thermal stability than many of the known adducts, but also a high volatility and lower melting temperature. Such characteristics significantly increase the utility of these complexes as source materials for chemical vapor deposition reactions.

BRIEF DESCRIPTION OF THE DRAWINGS

The invention may be further understood by reference to the drawings, wherein.

DETAILED DESCRIPTION

Figure 1:
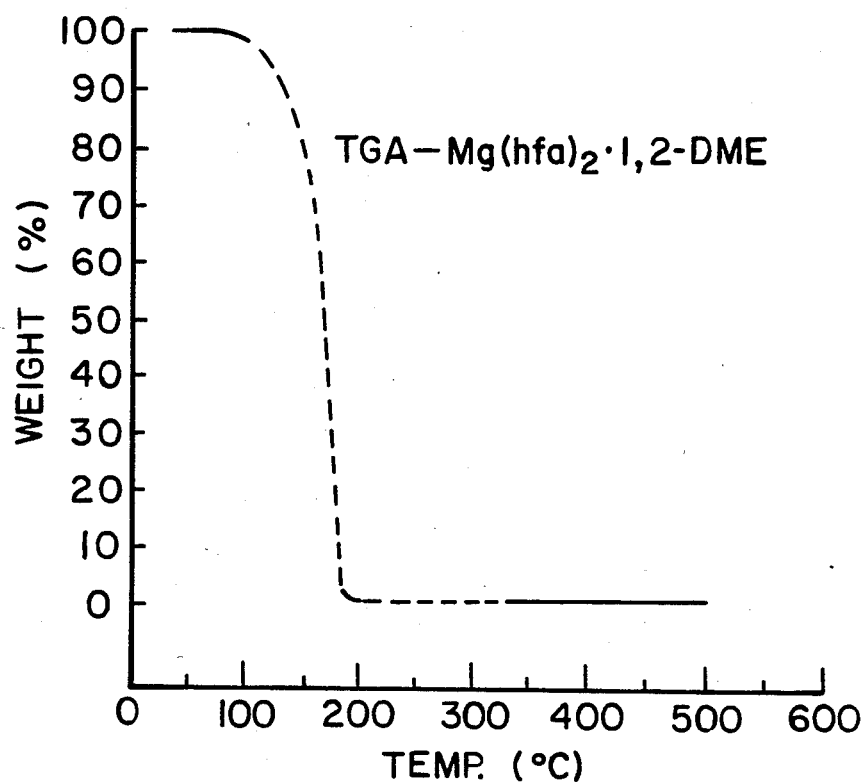
FIGS. 1 and 2 contain thermogravimetric curves for complexes provided according to the invention.

As is known, the volatility of metal β-diketonate complexes depends not only upon the selection of the diketone used to form the complex but also, for each possible diketone, upon the presence or absence and nature of the additional ligands (e.g., Lewis bases) present within the molecule. β-Diketonate complexes are known to form adducts with solvents used in their preparation, particularly when the complex is not coordinatively saturated and the solvent is a good Lewis base. These adducts can be relatively stable, and can be more volatile than the β-diketonate itself. Examples of molecules which can form adducts with metal β-diketonates are ammonia, water, ether, pyridine, bipyridine, phenanthroline, tetrahydrofuran and dimethylformamide. These molecules, termed neutral ligands, attach to the complex giving a metal atom with six-fold or higher coordination.

The stability of the metal β-diketonate adducts appears to depend on both the acidity of the β-diketonate and the base strength of the added molecule. The central metal atom of divalent metal β-diketonates such as $Zn(hfa)_2$ are known to exhibit significant electron affinity (Lewis acidity) due to the size of the metal atom and to the presence of the fluorine-containing β-diketonate ligands. Thus very stable adducts can be formed with some of the stronger Lewis bases. Particularly stable are adducts with certain of the nitrogenous bases.

Unfortunately stability alone is insufficient for qualification as a useful source material. As reported by Izumi et al., *Bull. Chem. Soc. Jap.*, 48(11), 3188 (1975), nitrogen-containing Lewis bases such as pyridine, 1,10-phenanthroline, and 2,2'-bipyridine form highly stable adducts with $M(hfa)_2$ β-diketonates, but these adducts can exhibit melting points significantly higher than some of the known adducts. A high melting point is undesirable in a metal source material. A low melting point and high volatility are greatly to be preferred, particularly where high mass transfer rates are needed.

The present invention is founded on the discovery that the 1,2-dimethoxyethane adducts of $Mg(hfa)_2$ and $Zn(hfa)_2$ exhibit improved stability and lower melting temperatures than previously known adducts of these complexes, but without sacrifice of volatility. Thus these 1,2-DME adducts, $M(hfa)_2 \cdot 1,2\text{-DME}$ can be volatilized rapidly and completely with lower risk of decomposition than can the parent complexes or other $M(hfa)_2$ adducts of the same diketonates, rendering them particularly useful, for example, as sources of metal vapors for vapor phase reactions.

The compound 1,2-dimethoxyethane($CH_3-O-CH_2-CH_2-O-CH_3$) is characterized as a bidentate ether with a boiling point of about 82° C. Adducts of this compound with the β-diketonates $Mg(hfa)_2$ and $Zn(hfa)_2$ can be prepared by synthesizing the β-diketonates as hydrates and then reacting the hydrates with the chelating bidentate ether. The resulting ether adduct can then be sublimed in vacuo without loss of the 1,2-DME ligand.

The following example describes a procedure useful for the synthesis of the $Mg(hfa)_2 \cdot 1,2\text{-DME}$ adduct.

EXAMPLE 1

$Mg(hfa)_2 1,2\text{-DME}$

To 1.6 liters of freshly distilled ether ($Et_2O$) in a three-necked flask is added 164 g of pure basic magnesium carbonate. The magnesium carbonate is commercially available as F.O. Optipur grade from E.M. Chemicals, Inc., Hawthorne, N.Y. The three-necked flask is equipped with a mechanical stirrer and provisions are made for maintaining an argon atmosphere over the reactants in the flask.

Hexafluoroacetylacetone($CF_3$—CO—$CH_2$—CO—$CF_3$) is distilled over $P_2O_5$ and 480 ml of the distilled β-diketone is added dropwise to the magnesium carbonate solution in the flask, with continuous stirring of the mixture. After completion of this addition and after the evolution of $CO_2$ from the reaction mixture ceases, the mixture is refluxed for 18 hours, cooled, and filtered. The ether is then removed by rotary evaporation to isolate the $Mg(hfa)_2.2H_2O$ intermediate hydrate.

This intermediate hydrate is next dissolved in excess 1,2-dimethoxyethane, and the resulting solution is gently refluxed for 16 hours to effect a replacement of the water of hydration by 1,2-DME. At the conclusion of this treatment, the excess 1,2-DME is removed by evaporation and the $Mg(hfa)_2.1,2$-DME product is sublimed in vacuo using a water-cooled sublimator. 740 g of $Mg(hfa)_2.1,2$-DME is recovered, for a yield of approximately 77%. The product has a melting point of 70° C., and has a vapor pressure of 10 mm (Hg) at about 120° C.

$Mg(hfa)_2.1,2$-DME produced by the above procedure has been characterized by chemical analysis, thermogravimetric analysis, Fourier transform infrared (FT-IR) analysis, and $^1H$ nuclear magnetic resonance (nmr) examination. Chemical analysis of the product for Mg, C, and H provided the results reported in Table I below. Included in the Table are experimental (analyzed) and calculated (theoretical) concentrations for these elements, reported in weight percent.

TABLE I

| Analysis of $Mg(hfa)_2.1,2$-DME | | |
|---|---|---|
| Element | Theoretical (%) | Analyzed (%) |
| Mg | 4.6 | 4.82 |
| C | 31.8 | 31.1, 31.3 |
| H | 2.3 | 2.3, 2.3 |

A thermogravimetric analysis (TGA) of the product was carried out on a 20 mg sample of the material, heated at a rate of 10° C./min under an argon atmosphere. A thermogravimetric curve resulting from such a study, identified as "TGA-$Mg(hfa)_2.1,2$-DME", is reproduced in FIG. 1 of the drawing. The TGA curve shows rapid and complete volatilization of the complex over a narrow temperature range, indicating the absence of detectable decomposition under the vaporization conditions employed. The temperature at which one-half of the sample has been evaporated ($T_{\frac{1}{2}}$), which temperature is a good relative indicator of the volatility of the compound, is estimated from the TGA curve to be about 170° C. This compares favorably with a $T_{\frac{1}{2}}$ temperature of 180° C. for $Mg(hfa)_2.2THF$.

Figure 3:
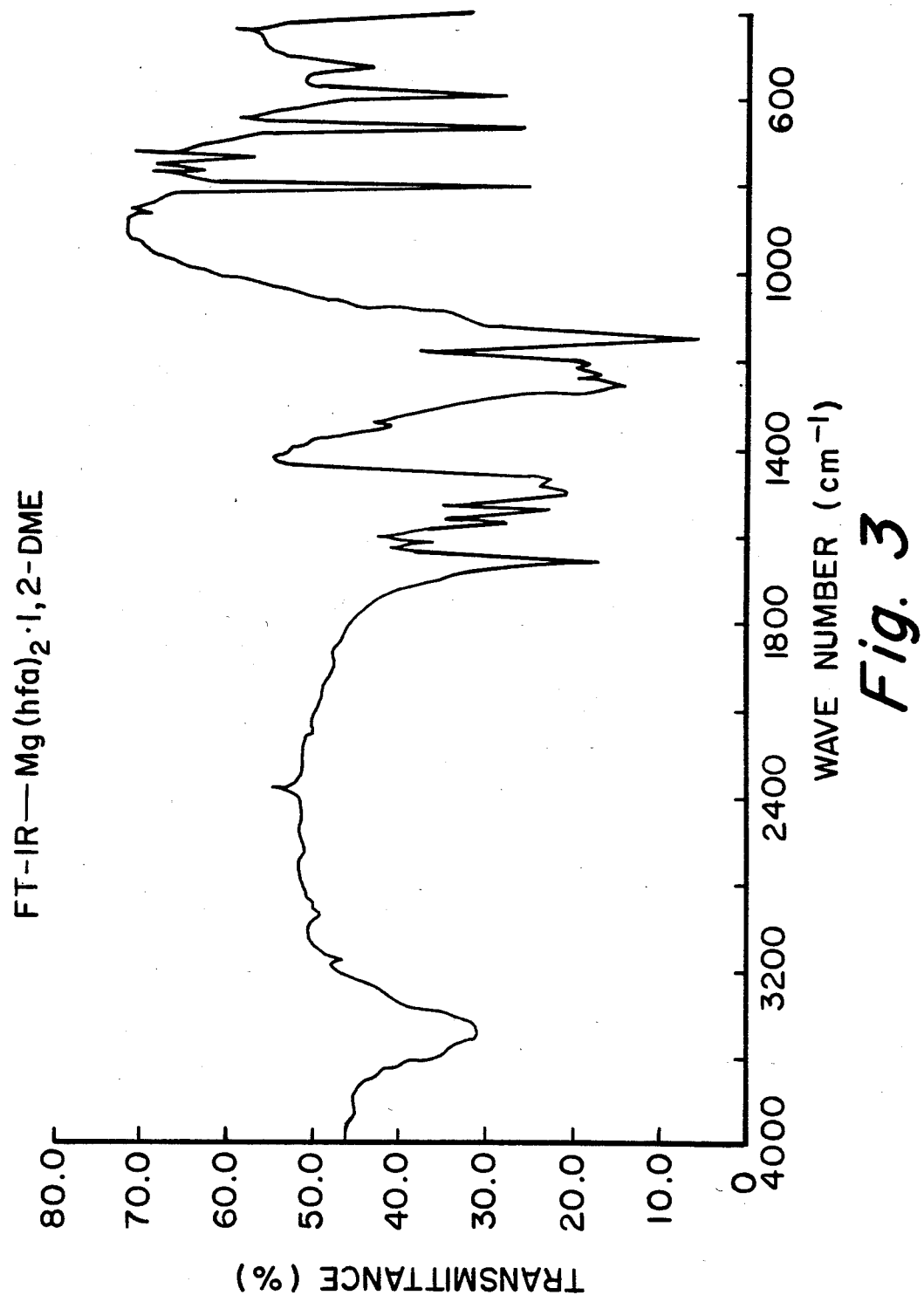
FIGS. 3 and 4 contain infrared transmittance spectra for complexes provided in accordance with the invention.

FIG. 3 of the drawing consists of an FT-IR spectrum of a $Mg(hfa)_2.1,2$-DME sample in potassium bromide. The spectrum is similar to that obtained at higher temperatures for the pure compound in the vapor phase.

Figure 5:
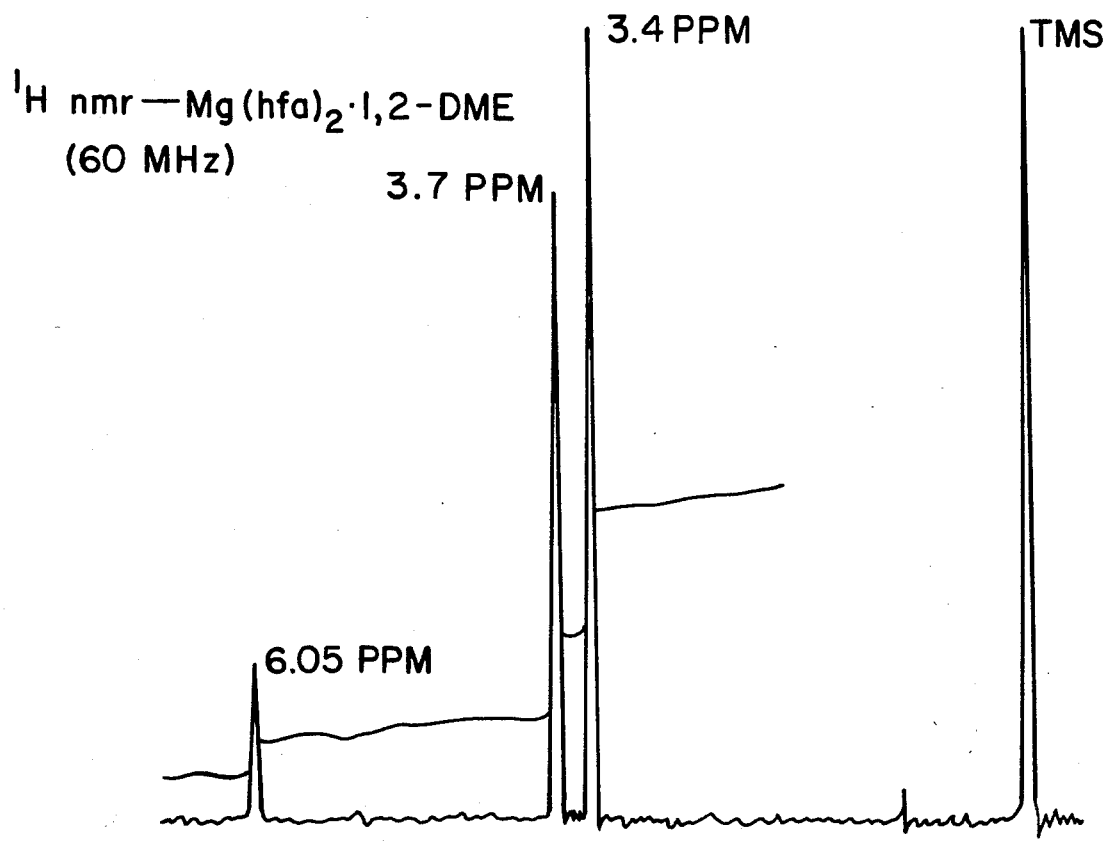
FIGS. 5 and 6 are proton nuclear magnetic resonance spectra for complexes provided in accordance with the invention.

FIG. 5 of the drawing consists of a $^1H$ nmr spectrum of an $Mg(hfa)_2.1,2$-DME sample in a $CD_2Cl_2$ solvent containing a tetramethylsilane (TMS) standard. The spectrum was generated on Varian model EM360L equipment. The resonance peaks at chemical shifts of 3.4 (intensity 6) and 3.7 ppm (intensity 4) are assigned to the 1,2-DME ligand, while the peak at 6.05 ppm (intensity 2) is assigned to the —CH group of the β-diketonate ligand. Electronic integration of the areas under the peaks support the proposed chemical formulation of one DME ligand per magnesium atom.

The thermal stability of $Mg(hfa)_2.1,2$-DME is evidenced not only by the TGA data set forth in FIG. 1, but also by investigations as to the extent and nature of the decomposition of $Mg(hfa)_2.1,2$-DME after prolonged heating at temperatures in the 100°–200° C. range. The superior thermal stability of the DME adduct was demonstrated by heating samples of the DME adduct and the THF adduct in individual evacuated ampoules at 200° C. for 24 hours and observing residual pressure in the ampoules after cooling to room temperature, and any sample discoloration which occurred. The DME adduct exhibits lower residual pressure after such a treatment than the corresponding bis-THF adduct, and also less discoloration.

The corresponding zinc adduct with the bidentate ether, $Zn(hfa)_2.1,2$-DME, can be prepared in a manner similar to that used for the preparation of the magnesium adduct according to Example I. The following Example describes such a procedure.

EXAMPLE 2

$Zn(hfa)_2.1,2$-DME

To a twelve-liter reaction vessel equipped with a stirrer, condenser, heating mantel, and a provision for argon purging are added 233 grams of pure (99.999%) zinc oxide and 800 ml of double-distilled water. Under an atmosphere of argon, 760 ml of 1,1,1,5,5,5-hexafluoracetylacetone, distilled as in Example 1, is slowly added with constant stirring. This addition is completed within about thirty minutes.

Two liters of diethyl ether is next added to the vessel, and the resulting mixture is gently heated for 80 hours. Thereafter the vessel and contents are allowed to cool, excess ZnO is removed by filtration, and the ether layer containing a dissolved $Zn(hfa)_22H_2O$ intermediate is separated from the water layer in a separatory funnel. Evaporation of this ether solution gives the hydrated zinc β-diketonate intermediate, $Zn(hfa)_2.2H_2O$.

The intermediate hydrate is next dissolved in excess hot 1,2-dimethoxyethane, and the resulting solution is refluxed for 16 hours at 68° C. to effect a replacement of the water of hydration with 1,2-DME. At the conclusion of this treatment, remaining excess 1,2-DME is removed by rotary evaporation and some of the $Zn(hfa)_2.1,2$-DME product is sublimed in a water-cooled sublimator to remove a small residual fraction of uncombined DME prior to product characterization.

The above process yields approximately 763 g of $Zn(hfa)_2.1,2$-DME, a yield of approximately 56%. The melting point of the sublimed $Zn(hfa)_2.1,2$-DME product is about 125° C., and this complex has a vapor pressure of about 16 mm (Hg) at 125° C.

$Zn(hfa)_2.1,2$-DME produced in accordance with the above-described procedure was analyzed for zinc, carbon, and hydrogen content with the results reported in Table II. Included in Table II are experimental (analyzed) and calculated (theoretical) concentrations for these elements, reported in weight percent.

TABLE II

| Analysis of Zn(hfa)₂.1,2-DME | | |
|---|---|---|
| Element | Theoretical (%) | Analyzed (%) |
| Zn | 11.5 | 11.1 |
| C | 29.5 | 29.3 |
| H | 2.1 | 2.0 |

Figure 2:
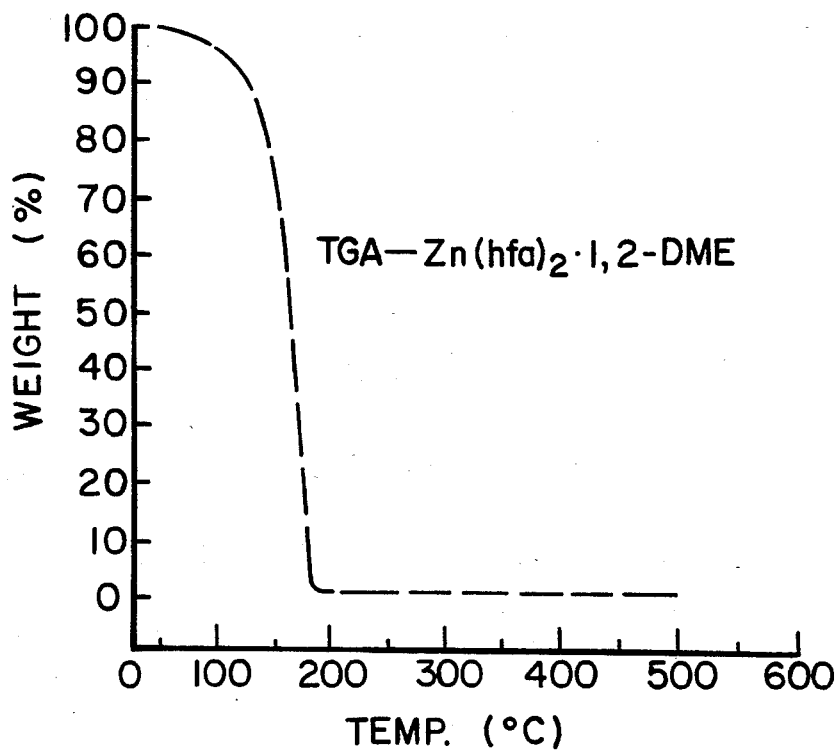

Thermogravimetric analysis of a sublimed 20 mg sample of the Zn(hfa)$_2$.1,2-DME product, heated at 10° C./min. under argon, resulted in the TGA curve shown in FIG. 2 of the drawing. As in the case of the magnesium complex, the zinc complex exhibits rapid and complete vaporization over a narrow range of temperatures, indicating no detectable thermal decomposition in the course of vaporization. The estimated $T_{\frac{1}{2}}$ temperature for the zinc complex under these conditions is 162° C., which is only slightly higher than the $T_{\frac{1}{2}}$ temperature of Zn(hfa)$_2$.2THF determined under the same conditions.

Figure 4:
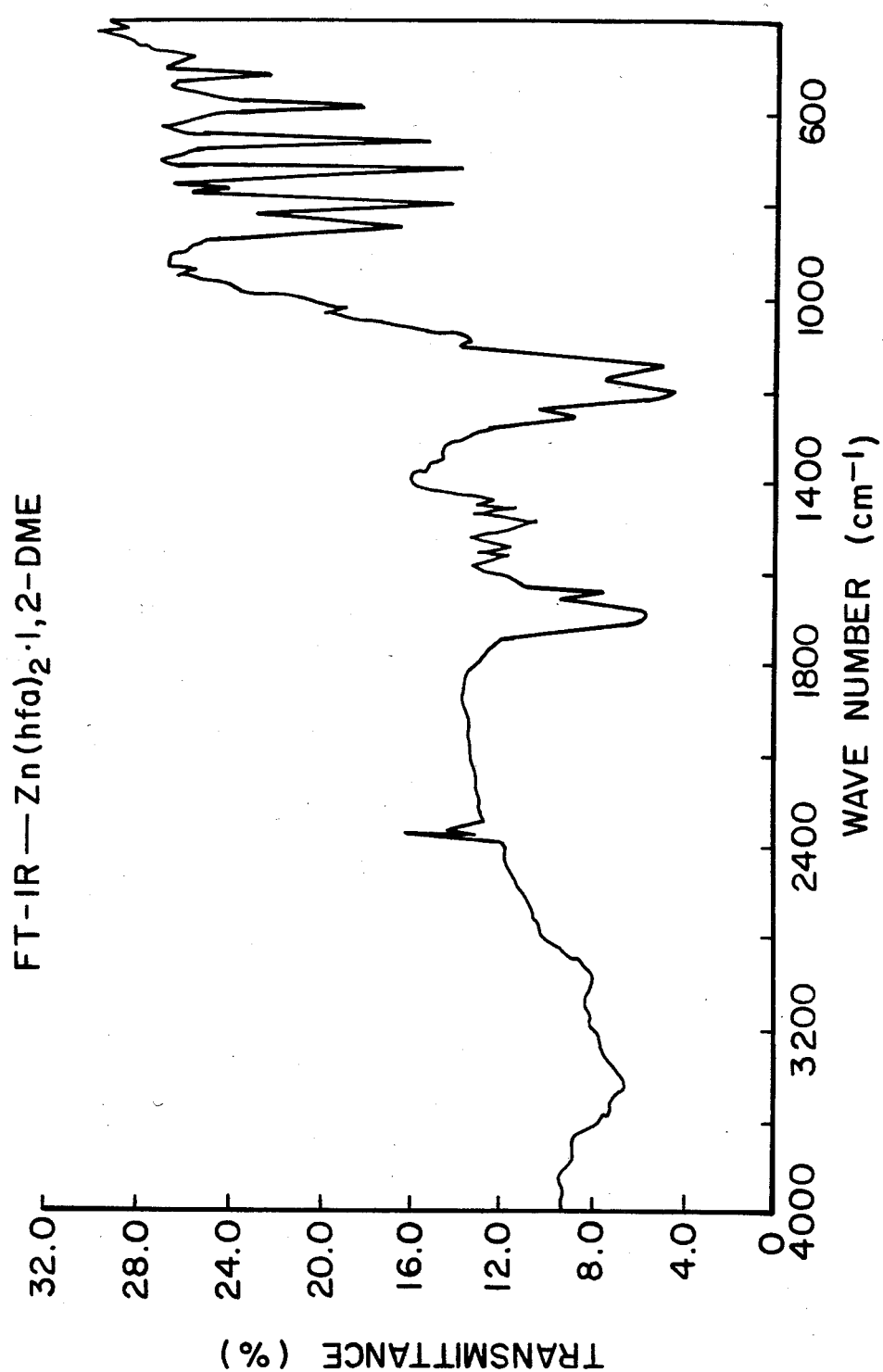

FIG. 4 of the drawing consists of an FT-IR spectrum exhibited by a sample of Zn(hfa)$_2$.1,2-DME between salt plates. That spectrum is similar to spectra obtained from vaporized Zn(hfa).1,2-DME at higher temperatures.

Figure 6:
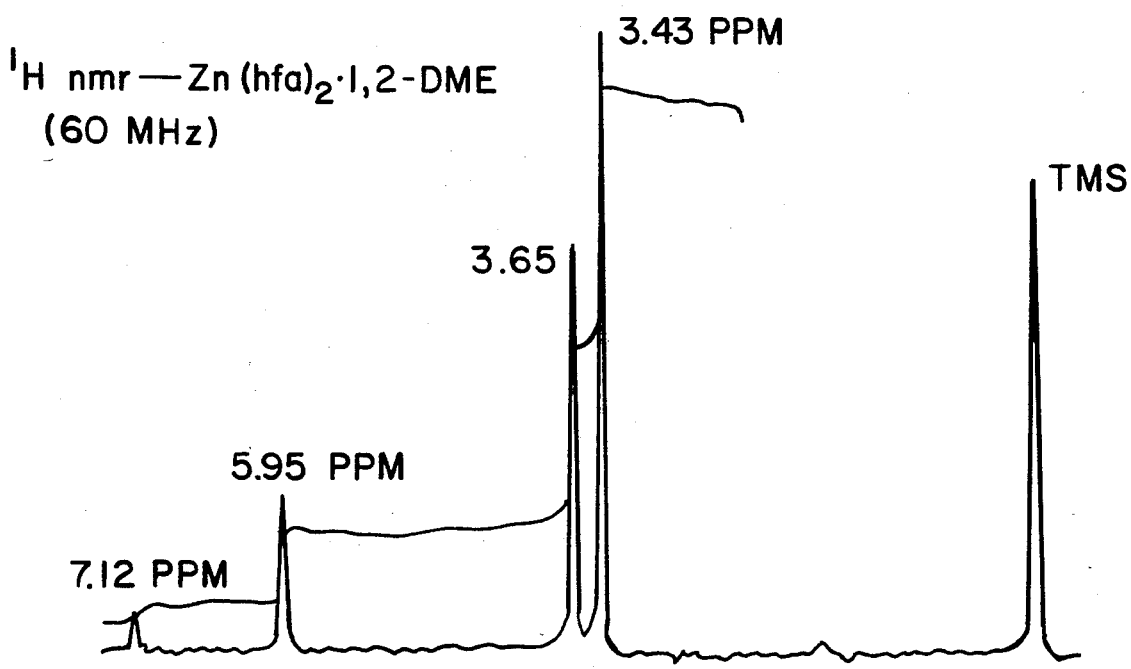

FIG. 6 of the drawing consists of an ¹H nmr spectrum of a Zn(hfa)$_2$.1,2-DME sample, dissolved in a CDCl$_3$ solvent which contained a TMS standard. The resonance peaks at chemical shifts of 3.43 and 3.65 ppm from the standard are assigned to the 1,2-DME ligand, while the peak at the 5.95 ppm chemical shift is assigned to the —CH group in the β-diketonate ligand. The small signal at 7.12 ppm is CHCl$_3$ impurity in the deuterated chloroform. Again, electronic integration of the areas under the peaks indicate one DME ligand per zinc atom.

As in the case of the magnesium complex, the thermal stability of Zn(hfa)$_2$.1,2-DME is evidenced not only by the observed rapid and complete TGA volatilization behavior shown in FIG. 2, but also by measuring residual gas pressure after heating a sample of the material in a sealed ampoule at 200° C. for 24 hours. Again the 1,2-DME adduct exhibits lower residual pressure and less discoloration after this test than the analogous THF adduct.

The combination of volatility and thermal stability exhibited by the M(hfa)$_2$.1,2-DME complexes of the invention appears to be unique. Attempts to produce stable complexes with other bidentate ethers such as 1,1-dimethoxyethane and 2,2-dimethoxypropane did not produce stable products. Further, addition complexes with the strongly coordinating nitrogen bases 1,10-phenanthroline and 2,2'-bipyridine, which are readily formed, failed to exhibit better properties than the 1,2-DME adduct.

Table III below sets forth comparative melting point and $T_{\frac{1}{2}}$ volatility data for 1,2-DME and nitrogen base adducts.

TABLE III

| Adduct | Melting Point - °C. | $T_{\frac{1}{2}}$ - °C. |
|---|---|---|
| Mg(hfa)$_2$.1,10-phenanthroline | 246 | 295 |
| Zn(hfa)$_2$.1,10-phenanthroline | 272 | 310 |
| Zn(hfa)$_2$.2,2'-bipyridine | 266 | 295 |
| Mg(hfa)$_2$.1,2-DME | 70 | 170 |
| Zn(hfa)$_2$.1,2-DME | 125 | 162 |

These data show a dramatic difference in volatility between the DME adducts and the adducts with strongly coordinating nitrogen bases of magnesium and zinc hexafluoroacetylacetonates, and demonstrate why the nitrogen adducts, although stable, are not good candidates for use as metal vapor source materials.

We claim:

1. The complex: M(hfa)$_2$.1,2-DME wherein M is Mg or Zn, hfa is 1,1,1,5,5,5-hexafluoro-2,4-pentanedionate, and 1,2-DME is the neutral 1,2-dimethoxyethane ligand.

2. A complex in accordance with claim 1 wherein M is Mg.

3. A complex in accorance with claim 1 wherein M is Zn.

* * * * *